United States Patent
Hoath et al.

(10) Patent No.: US 6,333,041 B1
(45) Date of Patent: *Dec. 25, 2001

(54) NONTOXIC VERNIX COMPOSITIONS AND METHOD OF PRODUCING

(75) Inventors: Steven B. Hoath; William L. Pickens; Martha O. Visscher, all of Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/447,108

(22) Filed: Nov. 22, 1999

Related U.S. Application Data (63) Continuation-in-part of application No. 09/257,008, filed on Feb. 25, 1999, which is a continuation-in-part of application No. 09/033,209, filed on Mar. 2, 1998, now Pat. No. 5,989,577.

(51) Int. Cl.$^7$ ........................................ A61K 7/00
(52) U.S. Cl. ........................ 424/401; 424/59; 514/844
(58) Field of Search ................. 424/401, 59; 514/844

(56) References Cited

U.S. PATENT DOCUMENTS

| | | |
|---|---|---|
| 3,655,416 | 4/1972 | Vinson et al. ............... 106/155 |
| 3,660,566 | 5/1972 | Vinson et al. ............... 424/95 |
| 4,366,169 | 12/1982 | White ........................... 424/285 |
| 4,428,965 | 1/1984 | Elsohly et al. .............. 424/311 |
| 4,451,453 | 5/1984 | Lay et al. ..................... 424/81 |
| 4,569,784 | 2/1986 | Moore ........................... 252/315.1 |
| 4,997,649 | 3/1991 | Papaconstantin et al. ........ 424/195.1 |
| 5,049,580 | 9/1991 | Crouthamel .................. 514/424 |
| 5,215,759 | 6/1993 | Mausner ....................... 424/489 |
| 5,540,964 | 7/1996 | Mallen ......................... 428/36.1 |
| 5,631,012 | 5/1997 | Shanni ......................... 424/401 |
| 5,871,763 | 2/1999 | Luu et al. .................... 424/402 |
| 5,874,091 | 2/1999 | Grollier ....................... 424/401 |

FOREIGN PATENT DOCUMENTS

| | | | |
|---|---|---|---|
| 0 440 058 | 7/1991 | (EP) | ............. A61K/7/00 |
| 2 614 787 | 11/1988 | (FR) | . |
| 1718947A1 | 1/1987 | (SU) | . |
| WO 98/01107 | 1/1998 | (WO) | ............. A61K/7/42 |

OTHER PUBLICATIONS

DM Eitzman, et al., Barrier membranes with tipped impermeable flakes., AlChE Journal [Supp], Jan. 1996, vol. 42, No. 1, 2–9.

V. M. Joglekar, Barrier properties of vernix caseosa, Archives of Disease in Childhood, vol. 55 (No. 10) 817–819, 1980.

WR Falla, et al., Estimating diffusion through flake–filled membranes., J of Membrane Science, 119 (1996) 129–138.

T Agorastos, M.C., et al., Features of Vernix Caseosa Cells, American Journal of Perinatology, vol. 5, No. 3, Jul. 1988.

N Nicolaides, et al., Further Studies of the Saturated Methyl Branched Fatty Acids of Vernix Caseosa Lipid, Lipids, vol. 11, No. 11.

(List continued on next page.)

Primary Examiner—Jose' G. Dees
Assistant Examiner—Konata M. George
(74) Attorney, Agent, or Firm—Wood, Herron & Evans, LLP (57) ABSTRACT

A composition containing vernix to provide therapeutic treatment in a human, and a method for using the composition, are disclosed. The composition may contain a natural or synthetic medicament, or may be manipulated to regulate transport properties. The medicament may be, for example, a protectant against ultraviolet radiation or an antioxidant. Various compositions and uses of vernix, both natural and synthetic, are disclosed. The compositions may be used in embodiments such as skin protection, wound healing, and restoration of epidermal barrier function.

53 Claims, 3 Drawing Sheets

OTHER PUBLICATIONS

SM Baker, et al., Is vernix a protective material to the newborn? A biochemical approach, Indian Journal of Pediatrics 1995, 62:237–239.

K Nakazawa, et al., Keratinocyte Extracellular Matrix–Mediated Regulation of Normal Human Melanocyte Functions, Pigment Cell Research, Feb. 1995, 8(1):10–18.

E Cussler, Membranes containing selective flakes., J. Membrane Sci., 1990, 52:275–288.

A Martin, *Rheology*, Physical Pharmacy, Physical Chemical Principles in the Pharmaceutical Sciences, Lea & Febinger, 4th Ed. 1993, Chapter 17 (pp. 453–476).

R Bree, Sonographic identification of fetal vernix in amniotic fluid., Journal of Clinical Ultrasound, 1978, 6(Aug.):269–270.

N Nicolaides, The Structures of the Branched Fatty Acids in the Wax Esters of Vernix Caseosa, Lipids vol. 6 No. 12.

JF Stadler, et al., Abstract, Topographical Variations of the Composition of Vernix Caseosa, Annual Meeting of the Dermatological Research Society, Nantes, France Oct. 9, 10, 11, 1986.

ME Stewart, Ph.D., et al., Variability in the Fatty Acid Composition of Wax Esters from Vernix Caseosa and Its Possible Relation to Sebaceous Gland Activity, The Journal of Investigative Dermatology, 78:291–295, 1982, vol. 78 No. 4.

NONTOXIC VERNIX COMPOSITIONS AND METHOD OF PRODUCING

RELATED APPLICATIONS

This application is a Continuation-In-Part of U.S. patent application Ser. No. 09/257,008 filed Feb. 25, 1999, which is a Continuation-In-Part of U.S. patent application Ser. No. 09/033,209 filed Mar. 2, 1998, now U.S. Pat. No. 5,989,577.

FIELD OF THE INVENTION

The invention relates generally to a therapeutic or prophylactic, natural or synthetic vernix film for enhanced growth and maturation of skin and other tissue.

BACKGROUND OF THE INVENTION

Skin is one of the largest organs in the body and covers substantially the entire body surface. Skin is composed of two main layers: the surface epithelium or epidermis which includes the uppermost stratum corneum, and the subjacent connective tissue layer or dermis. The skin has a number of functions such as protecting an organism from injury and dessication, receiving environmental stimuli, excreting various substances, regulating body temperature and helping to maintain water balance. Because of its quantitative and qualitative importance, substantially intact and healthy skin is crucial not only for the well being of an organism but for its very survival.

The health and integrity of skin may be compromised by wounds, abrasions, ulcers, burns, infections, irritations, premature birth and other conditions for which normal skin production and repair processes may be inadequate. For example, acute conditions such as in patients who are burned over a large surface area often require immediate skin replacement. Less life-threatening but chronic skin problems such as decubitus ulcers or irritations from diaper rash may progress to more severe conditions if left untreated or if they occur in a neonate or a geriatric patient. Skin treatments encompass a variety of methods and products. These may range from symptomatic treatments such as the use of topical anti-inflammatory compounds to the use of replacement skin. For various physiological, medical, and other reasons, however, none of these treatments meet the desired goal of utilizing the body's own healing and repair system to promote its own skin growth and maturation.

*Vernix caseosa* (vernix) is a naturally occurring skin protectant. Vernix is a lipid rich substance composed of sebum, epidermal lipids, and desquamated epithelial cells that covers the skin of the developing fetus in utero while the fetus is completely surrounded by amniotic fluid. Vernix consists of hydrated cells dispersed in a lipid matrix. This lipid matrix undergoes a transition to a more fluid form at physiological temperatures and with the application of shear forces, such as those encountered with movement. Vernix is a covering for the skin of the fetus that resembles the stratum corneum except that it lacks multiple rigid desmosomal connections. Consequently, vernix exhibits a viscous fluid character which allows vernix to act as a deformable, viscoelastic, semi-solid which coats the fetal skin surface before birth. This material detaches in part from the skin prior to birth and is swallowed by the developing fetus.

The lipid component of vernix has been reported in Stewart et al., *J. Invest. Dermatol.*, 78:291–295 (1982); Nicolaides, *Lipids* 6:901–905 (1972); Haahti et al., *J. Clin. & Lab. Investigation*, 13:70–73 (1961); Karkkainen et al.,*J. Invest. Dermatol*, 44:333–338 (1965); and U.S. Pat. No. 5,631,012, each of which is incorporated by reference herein in its entirety. Lipids, defined herein as fats or fat-like substances, include lecithin and other phospholipids, squalene, waxes, wax esters, sterol esters, diol esters, triglycerides, free sterols and four classes of fatty acids ranging in chain length from $C_{12}$ to $C_{26}$ (straight chain saturated, straight chain unsaturated, branched chain saturated, and branched chain unsaturated).

Because of its anticipated skin maturation and protectant properties, vernix appears to have promise as a clinically effective therapeutic agent. Application of vernix to clinical use, however, has been limited by its physical properties. While vernix in utero is a tractable semi-solid, vernix ex utero is a nonhomogeneous intractable compound with a consistency comparable to cheese or hardened cake frosting. Vernix is not completely soluble in conventional solvents such as absolute ethanol, 95% ethanol, 2-propanol, and combinations of chloroform and methanol. Thus, controlled and uniform administration of vernix to a surface is difficult. It has been reported that the surfactant polysorbate 80 (Tween 80) may solubilize vernix, but Tween 80 is toxic to living cells and therefore cannot be used clinically. Although there have been isolated reports of vernix directly scraped from a newborn baby for smearing over wounds (SU Patent No. 1718947A) or in an artificial lipid composition for use as a cosmetic moisturizer (U.S. Pat. No. 5,631,012), vernix in a therapeutic or prophylactic, natural or synthetic composition has not yet been reported.

While the barrier function and skin growth and maturational properties of vernix render it clinically useful to treat a variety of acute and chronic conditions, its physical properties have heretofore prevented its controlled administration in a clinical environment for therapeutic or prophylactic use. A need thus exists for a clinically useful vernix formulation and for a composition which can provide therapeutic treatment.

SUMMARY OF THE INVENTION

The invention is directed to a composition of vernix and a medicament. The vernix may be natural or synthetic. The medicament may be, for example, a protectant against ultraviolet (UV) radiation, a vitamin, a surfactant associated protein, a skin colorant, a nutrient, an antiinfective compound, or an immunogen.

The invention is also directed to methods for using the composition. One example is a method for protecting skin from exposure to UV radiation by applying an effective amount of a vernix/UV protectant composition in a pharmaceutically acceptable carrier to the skin. The UV protectant may be natural or synthetic, for example, melanin or para-amino benzoic acid. A second example is a method for altering skin coloration by applying an effective amount of a vernix/skin colorant composition in a pharmaceutically acceptable carrier to the skin. A third example is a method for protecting an epithelial surface from an oxidant by applying an effective amount of a vernix/antioxidant composition in a pharmaceutically acceptable carrier to the skin. The antioxidant may be a vitamin such as vitamin E. A fourth example is a method for providing a nutrient such as glutamine to a human. An effective amount of a vernix/nutrient composition in a pharmaceutically acceptable carrier is applied either parenterally or enterally.

The invention is also directed to a synthetic vernix composition having a lipid fraction in the range of about 5–15% by weight, a protein fraction in the range of about 5–15% by weight, and a medicament. The medicament may be a protectant against UV radiation, a skin colorant, an antioxidant, an antiinfective agent, an immunogen, and/or a nutrient.

The invention additionally includes a method of providing a spreadable composition of vernix and an effective amount of a surfactant associated protein in a pharmaceutically acceptable carrier to a surface, and a composition of vernix and surfactant associated protein B (SP-B) in an amount to enable the composition to be spreadably applied to a surface.

The invention is still further directed to a method of treating an epithelial surface. A composition containing an effective amount of vernix and a protein such as a surfactant associated protein, in a pharmaceutically acceptable carrier, is applied to the surface.

The invention additionally includes a method to regulate transport properties such as hydration in a biological surface. A vernix composition containing corneocytes is applied to the surface and the orientation of the corneocytes is altered, for example, by applying a shear stress. Regulation may include water transport within vernix, water release from vernix, permeability of one or more substances within vernix, release of one or more substances from vernix, and/or binding of one or more substances to vernix.

The invention also includes an antioxidant composition comprising vernix in a pharmaceutically acceptable carrier.

These and other methods and compositions will be apparent in light of the following figures and detailed description.

DETAILED DESCRIPTION OF THE PREFERRED EMBODIMENT

A nontoxic vernix film and composition, and methods of producing and using the film and composition as a therapeutic agent, for example, for the delivery of selected medicaments such as nutrients or other bioactive molecules, are described. A therapeutic agent or drug is defined as one that is used to treat a preexisting or impending condition or to affect a structure and/or function of the body. The treatment may be prophylactic, curative, protective, maturation enhancing or combinations of these. In contrast to a therapeutic agent, a cosmetic agent is defined as one that brings about an improved appearance but with no mandatory claims to efficacy.

Vernix compositions may be natural or synthetic. Natural vernix was obtained from a newborn infant at the time of delivery. Natural vernix comprises about a 10% lipid fraction by weight, about a 10% protein fraction by weight, and about an 80% volatile fraction by weight. The volatile fraction is primarily water. The rate of evaporation of volatile components is relatively slow, presumably due to the low rate of water vapor transmission through the lipid matrix or increased energy requirements for the dissociation of hydrogen bonds to change water from the liquid to the gaseous state. Vernix is an odorless material, again indicating the absence of volatile carbon or nitrogen containing compounds. At least a portion of the lipid and protein fraction are cellular components, for example, corneocytes. Natural vernix also contains calcium, tocopherols (vitamin E) of which α-tocopherol is the most potent and pulmonary surfactant associated proteins (SP) such as SP-A and SP-D.

A synthetic vernix composition may be partially synthetic or totally synthetic. Synthetic vernix comprises about a 5–15% lipid fraction by weight and about a 5–15% protein fraction by weight. In a hydrated state, there is about a 60–80% water fraction by weight. The water fraction may be removed to comprise as little as about 10% water, however, to prepare a partially or substantially dehydrated form of vernix. In one embodiment, a preservative may be added to the formulation. The preservatives that may be used in skin care formulations include benzoic acid, butylparaben, diazolidinyl urea, DMDM hydantoin, ethylparaben, imidazolidinyl urea, iodopropynl butylcarbamate, isobutylparaben, isopropylparaben, methyldibromo glutanitrite/phenoxyethanol, methylparaben, propylparaben, and quatermium-15.

As previously described, the lipid fraction of vernix has been reported to comprise lecithin and other phospholipids, squalene, waxes, wax esters, sterol esters, diol esters, triglycerides, free sterols and four classes of fatty acids ranging in chain length from $C_{12}$ to $C_{26}$ (straight chain saturated, straight chain unsaturated, branched chain saturated, and branched chain unsaturated). The lipid fraction may contain, with the relative percentages indicated, squalene (9%), aliphatic waxes (12%), sterol esters (33%), diesters (7%), triglycerides (26%), free sterols (9%), and other lipids (4%). The fatty acids within the aliphatic waxes may be branched and the branched fatty acids may be methylated. The protein fraction consists of epidermally derived proteins, primarily keratin and filaggrin. The protein fraction also contains trace amounts in the range of about micromolar to millimolar concentrations of regulatory proteins such as epidermal growth factor, and trace amounts of about nanomolar to micromolar concentrations of surfactant associated proteins such as SP-A and surfactant associated protein-B (SP-B) and surfactant associated protein-D (SP-D).

In utero, the developing fetus is exposed to an environment that prepares it for ex utero existence. Natural vernix, a unique embodiment of fetal skin exposed to the amniotic fluid, covers the developing fetus in the third trimester of pregnancy, with vernix that is sloughed off being swallowed by the developing fetus. Following birth, vernix is slowly detached from the skin of the infant as sebaceous gland secretion diminishes.

Pulmonary surfactant associated proteins also confer useful benefits on the developing fetus. Pulmonary surfactant is a phospholipid-protein mixture which reduces the surface tension of the lung and prevents collapse of the lung during air breathing. Prior to birth, surfactant synthesis by the lung results in the accumulation of both phospholipids such as lecithin, and specific surfactant proteins in the amniotic fluid. The most abundant protein in this mixture is a hydrophilic molecule termed surfactant-associated protein A (SP-A), but other surfactant associated proteins such as SP-B and SP-D are also present.

Pulmonary SP-A and SP-D belong to the collectin group of the C-type lectin superfamily. Other collectins include mannan-binding lectin, conglutinin, and collectin-43. SP-A binds phospholipids of pulmonary surfactant such as dipalmitoylphosphatidylcholine. SP-A, along with surfactant-associated protein D (SP-D), has antiinfective properties in that these surfactant associated proteins elicit macrophage phagocytosis, resulting in the destruction of microorganisms such as viruses, bacteria and fungi. As such, collectins such as SP-A and SP-D play key roles in the innate immune system of the lung, which is critical for immediate antibody-independent host defense.

Figure 1A:
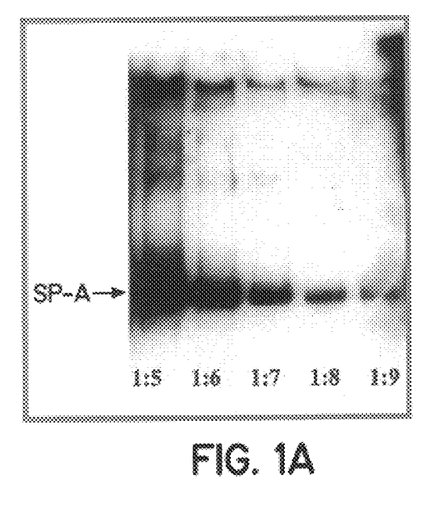
FIG. 1A is a photograph of a Western blot analysis demonstrating surfactant protein-A in vernix.
Figure 1B:
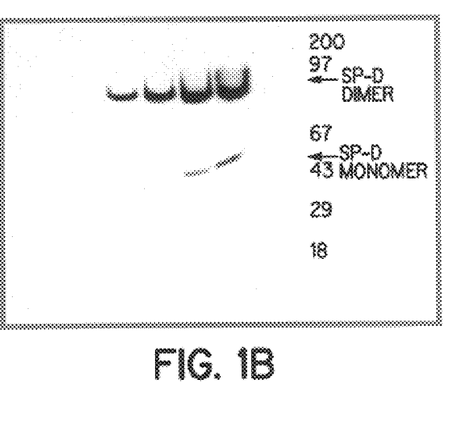
FIG. 1B is a photograph of a Western blot analysis demonstrating surfactant protein-D in vernix.

The role of pulmonary surfactant molecules as modulators of the rheological properties of vernix has been studied. With reference to FIG. 1, the presence of SP-A was demonstrated in serial dilutions of human vernix using Western blotting. Freshly obtained vernix was dispersed in standard polyacrylamide electrophoresis loading buffer containing sodium dodecyl sulfate. Serial dilutions of the mixture were subjected to electrophoresis on a polyacrylamide gel and immunoblotted with a $^{32}$P-labeled polyclonal antibody directed toward pulmonary SP-A.

The presence of SP-A and SP-D in native vernix, as shown in FIGS. 1A and 1B respectively, demonstrates that a specific protein of pulmonary origin combines with a barrier substance of cutaneous origin, to produce in utero a heterogeneous surface coating (i.e., vernix) with new properties important for barrier protection and host defense. The detachment of vernix from, and subsequent swallowing by, the fetus would hypothetically expose the fetal gut to the SP-A/vernix combination. This unique biology provides support for the use of natural or synthetic vernix as a delivery device for presenting SP-A or other collectin molecules of pulmonary or extrapulmonary origin to immature, wounded, or immunocompromised epithelial surfaces, such as the gut or skin.

However, little attention has been paid to vernix as a physiologically relevant surface active material. The presence of surfactant associated proteins such as SP-B in natural vernix, and the addition of SP-B and/or its derivatives to a synthetic vernix composition, permits control of the rheological properties of the composition. This is advantageous in a number of environments, such as when applying the composition to a natural or synthetic surface such as intact skin (e.g., as a barrier), compromised skin (e.g., as a wound treatment) or a synthetic surface (e.g., applied to a membrane, a film, a fabric, a wound dressing, an adhesive product, an ostomy care product, a hospital pad, an incontinent pad, an absorbent pad, an examination pad, a diaper and/or a feminine hygiene product).

Natural or synthetic vernix may be advantageously used as a vehicle for delivery of other substances due to its combined hydrophilic/hydrophobic character. Examples of substances to be delivered include, but are not limited to, required or supplemental nutrients, immunological molecules, therapeutic agents, etc. The properties of vernix that allow its use as a vehicle include selective sequestration of the active moieties in a hydrophobic domain such as the lipid matrix, or in a hydrophilic domain such as corneocytes. Regulation of the high water content of vernix and binding or release of water soluble moieties are putatively associated with the cellular component, while binding or release of phospholipid-binding moieties and/or hydrophobic molecules would be a function of interaction with the lipid matrix. A lipid formulation that lacks the cellular component is not vernix, but a composition containing both the cellular and lipid components of vernix, whether both components are natural, both are synthetic, or one component is natural and the other component is synthetic, may be used.

The cellular component of vernix, either of biologic or synthetic origin, may serve several functions. One function may be as an aid in the moisture delivery and/or moisture retention aspects of the disclosed composition. The high water content of vernix has been localized to the cellular component. Cells, for example skin epithelial cells in general and corneocytes in particular, may serve as vehicles for the slow release of water which supplies moisture to an appropriate tissue such as skin. Corneocytes, which are terminally differentiated skin cells, may be harvested from keratinocyte culture systems and may be incorporated into synthetic lipid formulations. The corneocytes may be bioengineered to perform a particular function or to provide a particular gene or gene product, as described in co-pending application Ser. No. 09/257,008 which is expressly incorporated by reference herein in its entirety.

Corneocytes are flattened discs measuring approximately 10–40 microns in diameter and 1–2 microns in thickness. In vivo, these cellular discs are embedded in a lipid matrix of presumptive sebaceous origin (e.g., see FIG. 3). The overall form of vernix, therefore, can be modeled as described for flake-filled membranes. The permeability properties of flake filled membranes have been investigated using inorganic flakes of mica, with value for use in transport across human skin as described by Falla et al. (Journal of Membrane Science 119, 1996, 129–138), which is expressly incorporated by reference herein in its entirety. The orientation of the flakes is a primary determinant of the permeability of such membranes and depends on several factors. The factor providing the chief contribution to the increased resistance in flake-filled barrier membranes is the resistance to diffusion of the tortuous path around the flakes (a "wiggle"). Other less important factors are the resistance to diffusion of the slits or gaps between adjacent flakes in the same horizontal plane (the "slit resistance"), and the constriction of the solute to pass into and out of the narrow slits ("necking"). Falla et al. mentioned the close parallel between the geometries used in simulating flake-filled membranes and human skin, remarking that the outermost layer of the skin (stratum corneum) consists of about twenty layers of keratin-rich cells embedded in a lipid bilayer matrix, with the impermeable keratin cells analogous to flakes and the lipid matrix corresponding to the continuum. Thus, the presence of the keratin-rich cells reduces the diffusion of materials through the lipid by three hundred times, with two thirds of this reduction due to wiggles and one third results from necking, with almost nothing from the slits between the flakes.

Figure 2A:
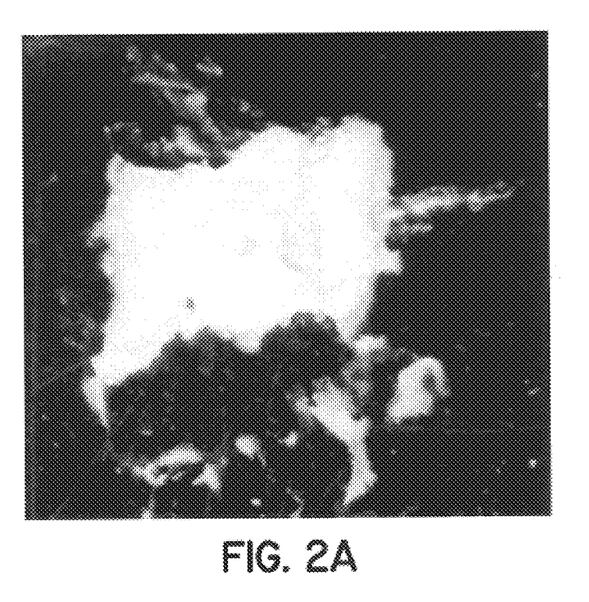
FIGS. 2A and 2B are photomicrographs showing two orientations of vernix.
Figure 2B:
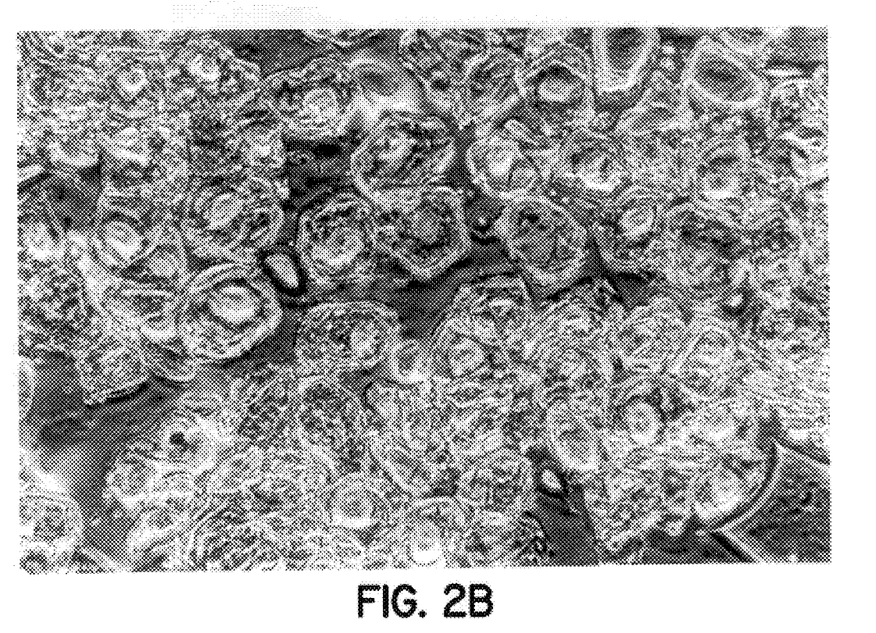
Figure 3:
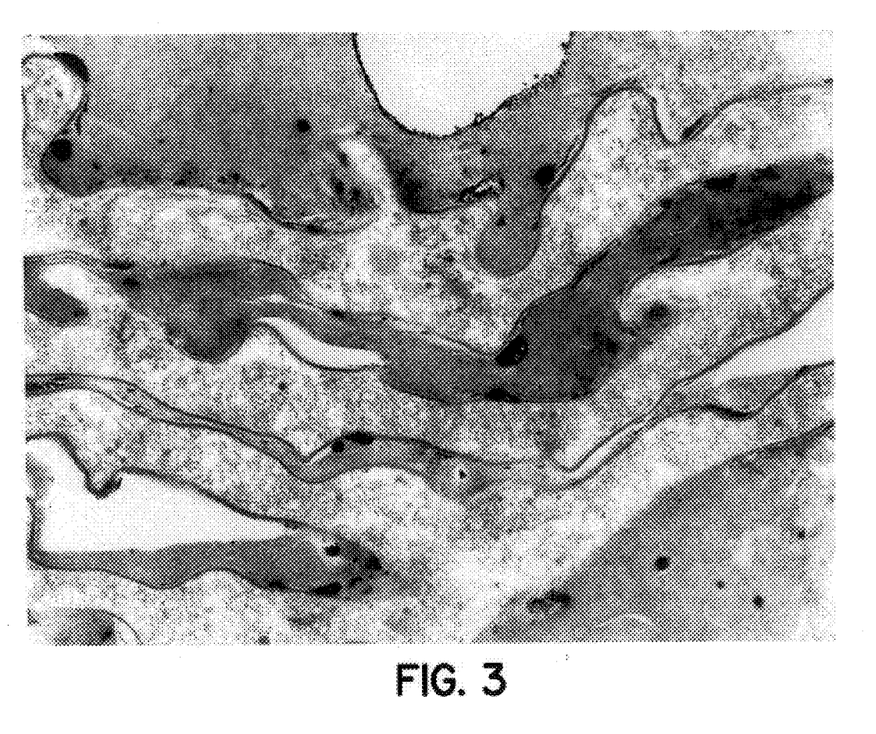
FIG. 3 is a transmission electron photomicrograph of vernix.

Vernix may be compared to mica-filled membranes but with the flakes constituted by biological units; i.e., corneocytes. Vernix is analogous to stratum corneum, but there are no desmosomal attachments between cells in vernix. These structural differences between vernix and stratum corneum confer novel properties upon vernix insofar as the application of exogenous directional stresses allow orientation of the corneocytes within vernix but not within the stratum corneum. Examples of such orientation are shown in FIGS. 2A and 2B. FIG. 2A shows freshly harvested vernix under low magnification (30×). Vernix is comprised of a large amount of sebaceous-derived wax esters and has the appearance and feel of a lipid material. FIG. 2B shows the same vernix sample flattened between two glass slides and viewed by phase contrast microscopy (500× magnification). Flattening of the vernix results in an oriented array of corneocytes lying parallel to the visual axis. There is dense packing of fetal corneocytes surrounded by a presumptive lipid matrix. Of particular note is the observation that vernix is primarily a cellular moiety. FIG. 3 is a transmission electron photomicrograph (21,000× magnification) of a flattened vernix sample. The large number of fetal corneocytes are shown as flattened light grey structures surrounded by the darker staining lipid matrix.

A novel application of this controlled cellular orientation concept is the slow release of substances from vernix or across vernix under the influence of repetitive shear stress. Repetitive shear stress would be exerted, for example, with directional massage or application of force to vernix. Application of shear force to a molecule such as a cell causes the molecular segments to align in the direction of shear. Viscous drag forces cause molecular segments to become stretched along their horizontal axes and compressed along their vertical axes. At low shear stresses, molecular segments are able to compress and stretch to dissipate energy, and considerable kinetic energy is converted into heat. Thus, the viscosity is high. At higher shear stresses, molecular segments become effectively rigid and do not transform as much kinetic energy into heat. Thus, the apparent viscosity decreases. At low shear stresses, thermal motion overcomes any tendency toward molecular alignment, but as the shear rate increases the molecules begin to disentangle and align, hence the resistance to flow past one cell to another is reduced. Under high shear stresses, the elements (cells) become almost totally disentangled and aligned. Thus, a steady state condition is reached where a minimum flow resistance occurs. Repetition of high shear stress would tend to further orient the molecular or cellular elements.

The rheological behavior of substances is explained in, e.g., Rheology, chapter 17 (p. 453–476 of Physical Pharmacy, Physical Chemical Principles in the Pharmaceutical Sciences, Alfred Martin, Lea & Febiger, $4_{th}$ Edition, 1993), which is expressly incorporated by reference herein in its entirety. The rheological (flow) behavior of vernix can be explained by the dynamics of entangling and disentangling of cellular elements. A sample of vernix was spread onto a plate of a Dynamic Stress Rheometer SR-5000® (cone and plate set, plate diameter 40 mm) (Rheometric Scientific, Inc., Piscataway, N.J.), with the plate adjusted to 25° C. The vernix sample was sufficient to cover the plate after the cone was lowered, leaving a gap of 0.046 mm between the cone and plate. A preshear stress of 500 dyne/cm$^2$ was applied before a steady stress sweep between 500–10,000 dyne/cm$^2$ was applied. The rheometer measured the shear strain and viscosity corresponding to the shear stress applied. The same vernix sample was subjected to a repetitive shear stress, with a one minute interval between five repetitions.

Figure 5:
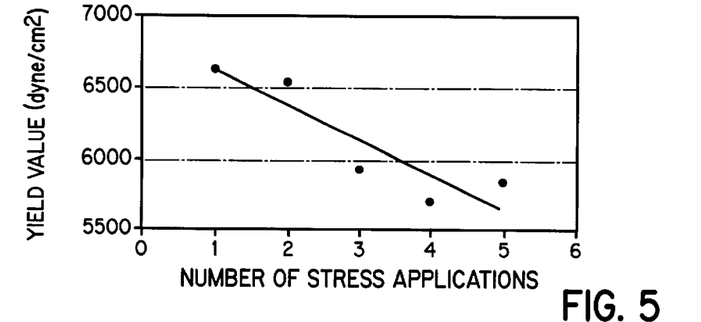
FIG. 5 is a graph showing a drop in yield value of vernix subjected to repetitive shear stress.

A stress-strain curve was plotted, as shown in FIG. 5. The drop in yield value, defined as the minimum amount of shear stress that must be applied for a material to begin flowing, was calculated. The fall in the yield value during repetitive stresses ($r^2$=0.80) shown in FIG. 5 is consistent with progressive alignment of cellular elements (analogous to mica flakes), with consequent lowering of the viscosity of the vernix sample.

Control of orientation of the cellular elements in vernix may have direct effects on several processes, given the mathematics of flake-filled membrane transport processes and the high water content of cells such as corneocytes. These transport properties, such as hydration-related processes, include water transport within vernix, water release from vernix, the permeability of substances within vernix, the release of substances from vernix, and the binding of substances to vernix. The effects may relate directly to the moisturizing properties of vernix and its ability to control water gradients across surfaces to which it is applied.

Substances within vernix or substances interacting with vernix may have anticipated therapeutic uses. An example of one nutritive use is supplementation with vernix containing glutamine. Glutamine is a water soluble, nonessential amino acid that is produced by the human body. Under specific circumstances, the availability of glutamine may be limited, in which case it becomes an essential amino acid. Glutamine is known, for example, to be an important nutrient for rapidly dividing cells such as cells from the immune system and the gut. One of the important functions of the gut is to prevent migration of bacteria and/or toxins from the gut lumen into the systemic circulation. A lack of glutamine may result in deterioration of this intestinal barrier. In the small intestine, glutamine is considered conditionally essential. Supplementation of glutamine to certain patients with immature or compromised small intestinal function could be essential.

In a report of the amino acid composition of a vernix hydrolysate (Baker et al., Indian Journal of Pediatrics 1995; 62:237), over one fifth (22.7±2.5%) of the free amino acids were glutamine. The authors noted the importance of this amino acid in lymphoblasts synthesizing immunoglobulin, and recommended that vernix be left intact on the newborn skin surface instead of following the usual practice of discarding the material as detritus. Since vernix detaches in part from the skin prior to birth and is swallowed by the developing fetus, the detachment process may be aided by the presence of surfactant material of pulmonary origin that is present in the amniotic fluid. In light of this information and given reports of the high glutamine content of vernix, there is likely a novel nutritive role for vernix. Thus, natural or synthetic vernix may provide a prototypical delivery device for glutamine and other endogenous or exogenous molecules beneficial to patients having immature, wounded or immunocompromised epithelial surfaces. Such patient populations would include, for example, premature infants, burn patients and patients with immunocompromised immune systems secondary to infection or cancer.

Figure 4A:
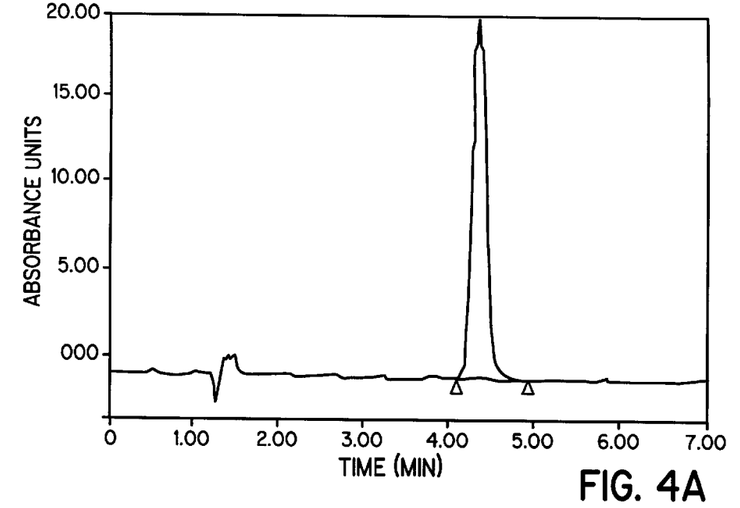
FIG. 4A is a chromatograph of a vitamin E standard.
Figure 4B:
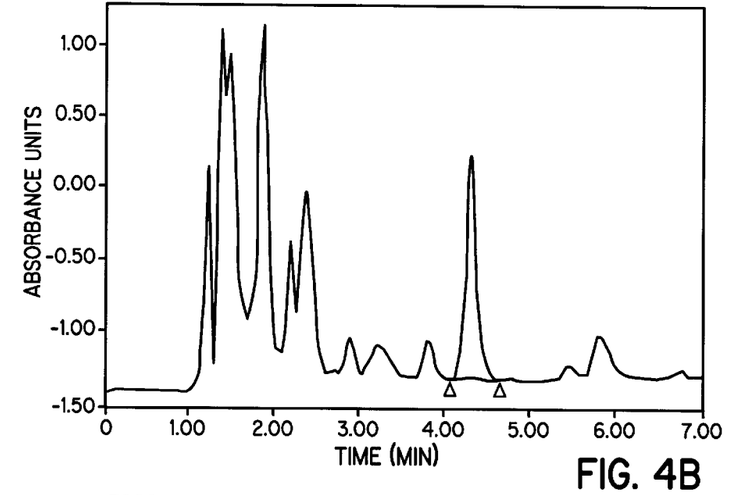
FIG. 4B is a chromatogram of a vernix extract.

A vernix composition may also function as a delivery or therapeutic vehicle for essential factors such as lipophilic vitamins (vitamins A, D, E, and K). Natural vernix contains the antioxidant vitamin E, as shown in FIGS. 4A and 4B. A sample of vernix was obtained from a newborn, and the hydrophobic components were extracted into chloroform. The chloroform was then evaporated and the residue was resuspended in 95% ethanol and centrifuged at 2000×g for 10 min. The supernatant was filtered through a 0.22 μm filter and injected onto an HPLC C-18 packed column. Substances were eluted using an isocratic gradient of 95% ethanol and fractions were monitored at an absorbance of 280 nm.

FIG. 4A is an HPLC absorbance chromatogram of a vitamin E standard that was recovered from the column using the previously described method. The retention time was about 4.4 min. FIG. 4B shows the extracted vernix composition. The chromatogram demonstrates a peak having a retention time of about 4.4 min, corresponding to the retention time of the vitamin E standard shown in FIG. 4A.

It is known (e.g., Devlin, Textbook of Biochemistry, Fourth Ed., Wiley-Liss, New York 1997) that vitamin E is lipophilic and accumulates in circulating lipoproteins, cellular membranes, and fat deposits. It reacts very rapidly with molecular oxygen and free radicals to scavenge for these compounds, protecting unsaturated fatty acids (especially those in cellular membranes) from peroxidation reactions. Vitamin E appears to play a role in cellular respiration, either by stabilizing coenzyme Q or by helping transfer electrons to coenzyme Q. It also appears to enhance heme synthesis by increasing the levels of y-aminolevulinic acid (ALA) synthetase and ALA dehydratase. Most of these vitamin E effects are thought to be an indirect effect of its antioxidant potential, rather than its actual participation as a coenzyme in any biochemical reactions.

Premature infants fed on formulas low in vitamin E sometimes develop a form of hemolytic anemia that can be corrected by vitamin E supplementation. Adults suffering from fat malabsorption show a decreased red blood cell survival time. Hence, vitamin E supplementation may be necessary with premature infants and in cases of fat malabsorption. In addition, studies have suggested that supplementation with at least 100 mg/day of vitamin E may decrease the risk of heart disease. This is well above the current recommended daily allowance and is far greater than can be obtained from even a very well balanced diet. These findings have rekindled the debate as to whether dietary recommendations should consider optimal levels of nutrients rather than the levels needed to prevent deficiency diseases. As a fat-soluble vitamin, E has the potential for toxicity. However, it does appear to be the least toxic of the fat-soluble vitamins, and no instances of toxicity have been reported at doses of 1600 mg/day or less.

Newborn infants are at special nutritional risk. In the first place, this is a period of very rapid growth, and needs for many nutrients are high. Some micronutrients, such as vitamin E, do not cross the placental membrane well and tissue stores are low in the newborn infant. The gastrointestinal tract may not be fully developed, leading to malabsorption problems (particularly with respect to the fat-soluble vitamins). The gastrointestinal tract is also sterile at birth and the intestinal flora that normally provide significant amounts of certain vitamins take several days to become established. If the infant is born prematurely, the nutritional risk is slightly greater, since the gastrointestinal tract will be less well developed and the tissue stores will be less. If infants must be maintained on oxygen, supplemental vitamin E may be beneficial.

A natural or synthetic vernix formulation may assist in providing vitamin E to individuals requiring supplementation as described above, or to those with an increased risk of oxidative exposure, for example, environmental workers in which additional protection against oxidation would be desirable. In both of these cases, delivery of nutrients or therapeutic agents such as vitamin E directly to epithelial surfaces such as skin or gut may be advantageous.

Vernix may also be used to protect skin against damage caused by exposure to ultraviolet (UV) light. As epidermal cells mature, they produce the keratin filament-aggregating protein known as filaggrin. Filaggrin subsequently undergoes proteolysis within the corneocyte to form natural moisturizing factor (NMF). NMF is a mixture of amino acids such as urocanic acid and pyrollidone carboxylic acid which function as natural humectants to bind water and plasticize the stratum corneum. Urocanic acid absorbs ultraviolet (UV) radiation, and additionally possesses immunomodulatory properties. Filaggrin proteolysis within the corneocytes of vernix would result in the liberation of NMF with production of urocanic acid.

Melanin, a naturally occurring material found in skin, is also able to absorb and scatter UV radiation. Incorporation of one or more medicaments such as melanin or other compounds into a natural or synthetic vernix to form a composition would confer UV-protective properties on the composition. Examples of UV-protectant compounds include para-amino benzoic acid, avobenzone(parsol 1789), benzophenone-3, octylmethoxycinnamate, octyl salicylate, oxybenzone, titanium dioxide, phenylbenzimidazole sulfonic acid, and/or homosalate. The concentration of melanin could be adjusted to optimize the UV-protectant effect of the composition. As one example, individuals who have suffered burns may require increased protection from exposure to UV radiation. Vernix compositions for use on burn patients may incorporate a higher concentration of melanin than compositions for use on other patients. As another example, individuals who are particularly sensitive to the effects of UV radiation, such as those with fair skin, may require enhanced protection from such exposure. As previously described, protection from UV radiation may also be enhanced by the inclusion of urocanic acid, one of the naturally-occurring breakdown products of filaggrin.

A native or synthetic vernix composition may also be used to control or alter pigmentation of the skin. There is considerable variation in the coloration of vernix, with vernix collected from infants of color often being darker than vernix obtained from lighter skinned infants. The variations most likely are due to differing amounts and/or forms of the pigment melanin, which is formed by enzymatic oxidation of the amino acid tyrosine found in vernix. The pigment-altering formulation could be used, for example, in the treatment of pigment cell pathology such as vitiligo, a skin disease characterized by the occurrence of whitish nonpigmented areas surrounded by hyperpigmented borders. The formulation could also be used as a skin complexion-altering preparation, either directly (e.g., tanning) or indirectly (e.g., added to topically applied barrier compositions to provide a non-greasy material that easily blends with natural skin).

To alter skin pigmentation, melanin is incorporated into a natural or synthetic vernix formulation. Melanin may be added in the form of either melanosomes, aggregates of melanosomes (melanosome complexes), free melanin, or small melanin granules (melanin dust) within a lipid matrix to produce a coloring agent. Alternatively, melanin may be incorporated directly into the cellular component of vernix by in vitro cell co-cultures of keratinocytes and melanocytes. For example, keratinocyte extracellular matrix-mediated regulation of normal human melanocyte functions has been reported (Pigment Cell Res. February 1995, 8(1):10–18, which is expressly incorporated by reference herein in its entirety).

In summary, the above-described inventive compositions and methods meet a current need for a versatile biocompatible substance for interacting with multiple epithelial systems. The inventive compositions and methods are based on novel biological mechanisms which occur in the human fetus, and which do not exist in the adult organism. Reapplication of these fetal mechanisms make available new potential biological delivery and regulatory systems.

A nontoxic vernix composition and film and methods of producing and using the composition and film are thus disclosed. In addition, a vernix dispersion and methods of producing and using the dispersion are disclosed. The compositions and methods of the invention may be used for skin cell maturation, for skin protection and coloration, for nutritive purposes, and for wound healing and/or repair. Other variations or embodiments of the invention will also be apparent to one of ordinary skill in the art from the above description and example. For example, a vernix composition may be formulated into a cream, such as a first aid cream, a cream for treating poison ivy or other forms of contact dermatitis, or a diaper rash cream. Thus, the forgoing embodiments are not to be construed as limiting the scope of this invention.

What is claimed is:

1. A composition comprising vernix and a medicament wherein vernix is selected from the group consisting of natural vernix and synthetic vernix, said natural vernix comprising about a 10% lipid fraction by weight, about a 10% protein fraction by weight, and about an 80% volatile fraction by weight, and said synthetic vernix comprising from about a 5% to about a 15% lipid fraction by weight, and from about a 5% to about a 15% protein fraction by weight.

2. The composition of claim 1 wherein the medicament is a protectant against ultraviolet radiation.

3. The composition of claim 2 wherein the protectant is selected from the group consisting of melanin, melanosomes, melanosome complexes, melanin dust, urocanic acid, para-amino benzoic acid, avobenzone(parsol 1789), benzophenone-3, octylmethoxycinnamate, octyl salicylate, oxybenzone, titanium dioxide, phenylbenzimidazole sulfonic acid, homosalate and combinations thereof.

4. The composition of claim 1 wherein the medicament is a vitamin.

5. The composition of claim 4 wherein the vitamin is selected from the group consisting of A, D, E, K and combinations thereof.

6. The composition of claim 1 wherein the medicament is a surfactant associated protein (SP).

7. The composition of claim 6 wherein the surfactant associated protein is selected from the group consisting of SP-A, SP-B, SP-D and combinations thereof.

8. The composition of claim 1 wherein the medicament is a skin colorant.

9. The composition of claim 8 wherein the skin colorant is selected from the group consisting of melanin, melanosomes, melanosome complexes, melanin dust and combinations thereof.

10. The composition of claim 1 wherein the medicament is a nutrient.

11. The composition of claim 10 wherein the nutrient is glutamine.

12. The composition of claim 1 wherein the medicament is an antiinfective compound.

13. The composition of claim 12 wherein the compound is a collectin.

14. The composition of claim 1 wherein the medicament is a compound to enhance immunocompetency.

15. The composition of claim 14 wherein the compound is a collectin.

16. A method for protecting skin from exposure to ultraviolet (UV) radiation comprising applying an effective amount of a composition comprising vermix and a UV protectant in a pharmaceutically acceptable carrier to the skin wherein vernix is selected from the group consisting of natural vernix and synthetic vernix, said natural vernix comprising about a 10% lipid fraction by weight, about a 10% protein fraction by weight, and about an 80% volatile fraction by weight, and said synthetic vernix comprising from about a 5% to about a 15% lipid fraction by weight, and from about a 5% to about a 15% protein fraction by weight.

17. The method of claim 16 wherein the UV protectant is selected from the group consisting of melanin, melanosomes, melanosome complexes, melanin dust, urocanic acid, para-amino benzoic acid, avobenzone(parsol 1789), benzophenone-3, octylmethoxycinnamate, octyl salicylate, oxybenzone, titanium dioxide, phenylbenzimidazole sulfonic acid, homosalate and combinations thereof.

18. A method for altering skin coloration comprising applying an effective amount of a composition comprising vernix and a skin colorant in a pharmaceutically acceptable carrier to the skin wherein vernix is selected from the group consisting of natural vernix and synthetic vernix, said natural vernix comprising about a 10% lipid fraction by weight, about a 10% protein fraction by weight, and about an 80% volatile fraction by weight, and said synthetic vernix comprising from about a 5% to about a 15% lipid fraction by weight, and from about a 5% to about a 15% protein fraction by weight.

19. The method of claim 18 wherein the colorant is selected from the group consisting of melanin, melanosomes, melanosome complexes, melanin dust and combinations thereof.

20. A method for protecting an epithelial surface from an oxidant comprising applying an effective amount of a composition comprising vernix and an antioxidant in a pharmaceutically acceptable carrier to the surface wherein vernix is selected from the group consisting of natural vernix and syntheticvernix, said natural vernix comprising about a 10% lipid fraction by weight, about a 10% protein fraction by weight, and about an 80% volatile fraction by weight, and said synthetic vernix comprising from about a 5% to about a 15% lipid fraction by weight, and from about a 5% to about a 15% protein fraction by weight.

21. The method of claim 20 wherein the antioxidant is a vitamin.

22. The method of claim 21 wherein the vitamin is selected from the group consisting of A, D, E, K and combinations thereof.

23. A method for providing a nutrient comprising providing an effective amount of a composition comprising vernix and the nutrient in a pharmaceutically acceptable carrier.

24. The method of claim 23 wherein the nutrient is glutamine.

25. The method of claim 23 wherein the nutrient is provided enterally or parenterally.

26. The method of claim 23 wherein the nutrient is provided topically.

27. A synthetic vernix composition having a lipid fraction in the range of about 5–15% by weight and a protein fraction in the range of about 5–15%by weight and further comprising a medicament.

28. The composition of claim 27 wherein the medicament is selected from the group consisting of a protectant against ultraviolet (UV) radiation, a skin colorant, an antioxidant, an antiinfective, an immunogen, a nutrient and combinations thereof.

29. The composition of claim 28 wherein the UV protectant is selected from the group consisting of melanin, melanosomes, melanosome complexes, melanin dust, urocanic acid, para-amino benzoic acid, avobenzone(parsol 1789), benzophenone-3, octylmethoxycinnamate, octyl salicylate, oxybenzone, titanium dioxide, phenylbenzimidazole sulfonic acid, homosalate and combinations thereof.

30. The composition of claim 27 wherein the antioxidant is a vitamin.

31. The composition of claim 30 wherein the vitamin is selected from the group consisting of A, D, E, K and combinations thereof.

32. The composition of claim 28 wherein the antiinfective is a surfactant associated protein.

33. The composition of claim 32 wherein the surfactant associated protein is selected from the group consisting of surfactant associated protein A (SP-A), SP-B, SP-D and combinations thereof.

34. The composition of claim 28 wherein the skin colorant is selected from the group consisting of melanin, melanosomes, melanosome complexes, melanin dust and combinations thereof.

35. The composition of claim 28 wherein the nutrient is glutamine.

36. The composition of claim 28 wherein the antiinfective compound is a collectin.

37. A method of providing a spreadable composition comprising vernix and an effective amount of a surfactant associated protein in a pharmaceutically acceptable carrier to a surface.

38. The method of claim 37 wherein the surfactant associated protein is surfactant associated protein-B.

39. A composition comprising vernix and surfactant associated protein B (SP-B) in an amount to spreadably apply said composition to a surface.

40. The composition of claim 39 further comprising a collectin.

41. The composition of claim 39 wherein the surface is selected from the group consisting of a membrane, a film, a fabric, a wound dressing, an adhesive product, an ostomy care product, a hospital pad, an incontinent pad, an absorbent pad, an examination pad, a diaper, a feminine hygiene product and combinations thereof.

42. A method of treating an epithelial surface by applying a composition comprising an effective amount of vernix and a protein of pulmonary origin in a pharmaceutically acceptable carrier to the surface.

43. The method of claim 42 wherein said protein is a surfactant associated protein.

44. The method of claim 42 wherein said surface is a wound.

45. The method of claim 42 wherein said surface is immunocompromised.

46. The method of claim 42 wherein said surface is an immature organ selected from the group consisting of gut, skin and combinations thereof.

47. The method of claim 42 wherein said treatment restores a compromised epidermal barrier function.

48. The method of claim 42 wherein said composition is applied directly to said surface.

49. A method to regulate transport in a biological surface comprising applying a vernix composition containing corneocytes to said surface for orientating the corneocytes in the composition.

50. The method of claim 49 wherein transport regulation is selected from the group consisting of water transport within vernix, water release from vernix, permeability of at least one substance within vernix, release of at least one substance from vernix, binding of at least one substance to vernix and combinations thereof.

51. The method of claim 49 wherein transport regulation is by applying a stress to said composition.

52. An antioxidant composition comprising vernix in a pharmaceutically acceptable carrier wherein vernix is selected from the group consisting of natural vernix and synthetic vernix, said natural vernix comprising about a 10% lipid fraction by weight, about a 10% protein fraction by weight, and about an 80% volatile fraction by weight, and said synthetic vernix comprising from about a 5% to about a 15% lipid fraction by weight, and from about a 5% to about a 15% protein fraction by weight.

53. The composition of claim 52 further comprising vitamin E.

* * * * *